United States Patent [19]
Tahara et al.

[11] 4,183,666
[45] Jan. 15, 1980

[54] METHOD OF MEASURING LIGHT TRANSMISSION LOSSES OF OPTICAL MATERIALS

[75] Inventors: Yasuteru Tahara; Shunsuke Minami; Masaharu Oda; Mikio Sera, all of Otake, Japan

[73] Assignee: Mitsubishi Rayon Company, Limited, Tokyo, Japan

[21] Appl. No.: 776,171

[22] Filed: Mar. 10, 1977

[51] Int. Cl.² .............................................. G01N 21/00
[52] U.S. Cl. .................................. 356/73.1; 356/432
[58] Field of Search ................. 356/201, 206, 73.1, 356/432

[56] References Cited
U.S. PATENT DOCUMENTS

| | | | |
|---|---|---|---|
| 3,652,850 | 3/1972 | Briggs | 356/206 |
| 4,017,193 | 4/1977 | Loiterman | 356/206 |
| 4,037,973 | 7/1977 | Carr | 356/206 |
| 4,081,258 | 3/1978 | Goell et al. | 356/201 |

OTHER PUBLICATIONS

"Loss Mechanisms & Measurements in Clad Glass Fibers & Balk Glass," Tynes et al., JOSA, vol. 61 #2, Feb. 71, pp. 143–153.

*Primary Examiner*—Vincent P. McGraw
*Attorney, Agent, or Firm*—Oblon, Fisher, Spivak, McClelland & Maier

[57] ABSTRACT

A method of measuring light transmission losses of optical materials comprising projecting light beams at two separate points alternatively or a light beam through a part of an optical material to be measured, and detecting the intensities of light radiated at two separate points lying along the direction of propagation of said light beams in said part.

5 Claims, 3 Drawing Figures

METHOD OF MEASURING LIGHT TRANSMISSION LOSSES OF OPTICAL MATERIALS

BACKGROUND OF THE INVENTION

1. Field of the Invention

This invention relates to improvements in methods of measuring light transmission losses of optical materials, and more particularly of optical fibers.

2. Description of the Prior Art

Light transmission losses of optical fibers have been measured by methods such as that shown in FIG. 1. In said drawing, light from a lamp 36 is projected into an optical fiber 35 from one end surface 43, is projected out of the other end surface 44, is condensed by an integrating sphere 37, and is converted to an electric quantity by a photoelectric converting element 40, the electric quantity is amplified by an amplifier 41 and its output of amplifier is read out on an indicator 42. This value is denoted by $E_1$. Then the optical fiber is cut in a position 45 separated from the end surface 44 by a length L measured along the axis of the optical fiber 35. Then the new end surface 45 is fixed in the same position as the end surface 44 by a holder 39 and the indicated value of the indicator 42 is read out. This value is denoted by $E_2$.

The light transmission loss (absorption coefficient) can be determined from $E_1$ and $E_2$ by applying formula (1), having the form of the Lambert-Beer's law:

$$I_1 = I_2 \exp(-KL) \quad (1)$$

where
$I_1$: Intensity of the light at the end surface 44.
$I_2$: Intensity of the light at the end surface 45.
$K$: Light transmission loss (absorption coefficient).
$L$: Length of the cut optical fiber.
$I_1$ and $I_2$ are related respectively to $E_1$ and $E_2$ by the following formulas:

$$E_1 = (1-\rho_1)I_1 \quad (2)$$

$$E_2 = (1-\rho_2)I_2 \quad (3)$$

where
$\rho_1$: Reflection coefficient of the end surface 44.
$\rho_2$: Reflection coefficient of the end surface 45.

When formulas (2) and (3) are substituted in formula (1), formula (4) is obtained:

$$K = 1/L\{\ln(E_2/E_1) + \ln(1-\rho_1)/(1-\rho_2)\} \quad (4)$$

If the end surfaces 44 and 45 are cut and/or finished so that $\rho_1$ and $\rho_2$ are equal to each other, the light transmission loss may be determined from the following formula (5):

$$K = 1/L \ln(E_2/E_1) \quad (5)$$

Such a conventional method has demerits, in that the cut optical material cannot be used as a product, hence the method cannot be used to test all the products, in that it is not easy to cut or grind and finish the material so that the reflection coefficient of the cut surfaces are equal to each other, and in that the measurement requires a long time.

SUMMARY OF THE INVENTION

The object of the present invention is to provide a method of measuring light transmission losses wherein the above-mentioned defects of the conventional method are obviated. A further object of the present invention is to provide a method of measuring light transmission losses in optical fibers that does not necessitate cutting and/or finishing the fibers.

Another object of a preferred embodiment of the present invention is to provide a method of measuring light transmission losses in optical fibers that is adaptable to continuous operation while running the optical fiber.

These objects have been attained by providing a method of measuring light transmission losses of optical materials comprising projecting light beams at two separate points alternatively or a light beam through a part of an optical material to be measured, and detecting the intensities of light radiated at two separate points lying along the direction of propagation of said light beams in said part.

BRIEF DESCRIPTION OF THE DRAWINGS

A more complete appreciation of the invention and many of the attendant advantages thereof will be readily obtained as the same becomes better understood by reference to the following detailed description which considered in connection with the accompanying drawings, wherein:

In FIGS. 1 to 3, 1 is an optical fiber, 2 and 3 are lamps, 4 and 5 are integrating sphere, 6 and 7 are photoelectric converting elements, 8 and 9 are amplifiers, 10 and 11 are indicators, 12 is an optical fiber, 13 is a winding bobbin for an original optical fiber, 14 is a winding bobbin for a measured optical fiber, 15 is a pair of nipping rollers, 16 and 17 are lamps, 18 and 19 are choppers, 20 and 21 are condensers, 22 and 23 are light projecting part covers, 24 and 25 are integrating sphere, 26 and 27 are photoelectric converting elements, 28 and 29 are amplifiers, 30 is an analogue computer, 31 is a recorder, 32 is a measuring part cover, 33 and 34 are light projecting parts, 35 is an optical fiber, 36 is a lamp, 37 is an integrating sphere, 38 and 39 are fiber holders, 40 is a photoelectric converting element, 41 is an amplifier, 42 is an indicator and 43, 44 and 45 are fiber end surfaces.

DETAILED DESCRIPTION OF THE PREFERRED EMBODIMENTS

The present invention will now be explained in detail.

In the case of an ideal optical fiber, when a pencil of light with a cone angle smaller than the acceptance angle of the fiber is projected into the optical fiber from its one end surface, the incident light will be transmitted to the other end with multiple total reflections. In such case, no light will be radiated out of the optical fiber. It is also true that, even if the optical fiber is illuminated from the outside, other than from both end surfaces of the fiber, no light transmitting with multiple total reflections in the fiber may be generated.

However, a real optical fiber will contain varying amounts of such scattering elements as impurities and bubbles and therefore the light projected upon the end surface will be transmitted with radiation of small amounts of light out of the optical fiber. The amount of light radiated out will be proportional to the amount of incident light and will be measurable in practice. Further, by illuminating out of the surface of optical fiber from outside with a strong light source, the propagating light can be injected into the fiber wherein it can undergo multiple essentially total reflections.

Figure 1:
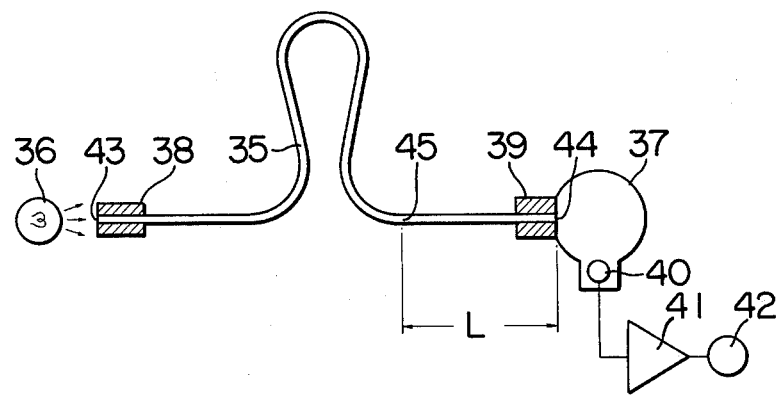
FIG. 1 is a vertically sectioned side view of a conventional apparatus to be used for measuring light transmission losses of optical fibers.
Figure 2:
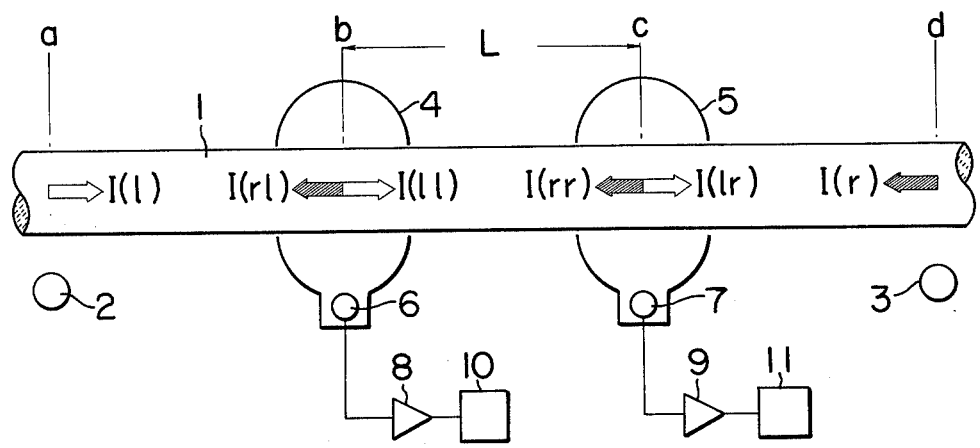
FIG. 2 is a partly vertically sectioned side view of an apparatus showing the principle of the present invention.

The present invention will be described in detail with reference to FIG. 2 which represents an optical fiber having such characteristics. In FIG. 2, 1 is an optical fiber, 2 is a lamp (left), 3 is a lamp (right), 4 is an integrating sphere (left), 5 is an integrating sphere (right), 6 and 7 are photoelectric converting elements, 8 and 9 are amplifiers, 10 is an indicator (left) and 11 is an indicator (right). I (l) is the intensity of light propagating rightward through a cross-section a through which the light is projected when the lamp 3 is turned off and the lamp 2 is turned on. I (ll) and I (lr) are, respectively, the average light intensities within the optical fiber in the parts enclosed by the respective integrating sphere when I (l) propagates to the integrating sphere 4 and 5. I (r) is the intensity of light propagating leftward through a cross-section d through which the light is projected when the lamp 2 is turned off and the lamp 3 is turned on. I (rr) and I (rl) are, respectively, the average light intensities within the optical fiber in the parts enclosed by the respective integrating sphere when I (r) propagates to the integrating bulbs 5 and 4. L is a length measured along the axis of the optical fiber between the center line b of the integrating sphere 4 and the center line c of the integrating sphere 5.

The case where lamp 2 is turned on, and lamp 3 is turned off, and the light I (l) is projected will be described first. In this case, too, the above-mentioned Lambert-Beer's law will hold and the following formula will be obtained:

$$I(lr) = I(ll) \exp(-KL) \tag{6}$$

where

K: Light transmission loss (absorption coefficient) of the optical fiber between the cross-sections b and c.

I (ll) and I (lr) are intensities of the light within the optical fiber and therefore cannot be directly measured. But the scattering light radiated out of the optical fiber due to the scattering elements contained in the optical fiber is proportional to I (ll) and I (rr) and can be condensed by the respective integrating sphere. These scattering light in the respective integrating sphere are converted to electric quantities by the respective photoelectric converting elements 6 and 7, amplified by the respective amplifiers 8 and 9, and read out as amounts E (ll) and E (lr), respectively, proportional to the light amounts, by the respective indicators 10 and 11. E (ll) and E (lr) may be expressed as follows:

$$E(ll) = \alpha(l) \times I(ll) \tag{7}$$

$$E(lr) = \alpha(r) \times I(lr) \tag{8}$$

where $\alpha(l)$ and $\alpha(r)$ named as general photoelectric conversion efficiency are represented by the following formula, respectively:

$$\alpha(l) = \beta(l) \times \gamma(l) \times \delta(l) \times \epsilon(l) \tag{9}$$

$$\alpha(r) = \beta(r) \times \gamma(r) \times \delta(r) \times \epsilon(r) \tag{10}$$

where $\beta(l)$: Efficiency of radiating the scattering light out of the optical fiber in the part enclosed with the integrating sphere 4.

$\beta(r)$: Efficiency of radiating the scattering light out of the optical fiber in the part enclosed with the integrating sphere 5.

$\gamma(l)$: Light condensing efficiency of the integrating sphere 4.

$\gamma(r)$: Light condensing efficiency of the integrating sphere 5.

$\delta(l)$: Converting efficiency of the photoelectric converting element 6.

$\delta(r)$: Converting efficiency of the photoelectric converting element 7.

$\epsilon(l)$: Gain of the amplifier 8.

$\epsilon(r)$: Gain of the amplifier 9.

$\beta(l)$ and $\beta(r)$ are determined by the scattering elements and usually fluctuating with the location of the optical fiber. $\gamma(l)$, $\gamma(r)$, $\delta(l)$, $\epsilon(l)$ and $\epsilon(r)$ are the apparatus constants and are substantially invariant. Therefore, $\alpha(l)$ and $\alpha(r)$ become dependent only upon the location of the optical fiber. However, in case it is not necessary to measure the transmission loss with high precision, $\alpha(l) = \alpha(r)$ may be assumed, and formula (11), obtained by substituting formulas (7) and (8) in formula (6), and where now in $\alpha(r)/\alpha(l) = 0$, simplifies to formula (11)' from which the light transmission loss K may be easily obtained:

$$K = 1/L \{\ln E(ll)/E(lr) + \ln (\alpha(r)/\alpha(l))\} \tag{11}$$

$$K = 1/L \{\ln E(ll)/E(lr)\} \tag{11}'$$

However, in case it is necessary to measure the light transmission loss with high precision, $\alpha(l)$ and $\alpha(r)$ will have to be taken into consideration.

The present inventors have discovered that $\alpha(l)$ and $\alpha(r)$ in equation (11) are eliminated by projecting into the fibers the light propagating in the opposite directions to that of I (l) and measuring that as in the previous case. That is to say, when lamp 3 is turned on and lamp 2 is turned off, the light I(r) is projected into the fiber in the same manner with that of I (l), the following formulas will hold:

$$I(rl) = I(rr) \exp(-KL) \tag{12}$$

$$E(rr) = \alpha(r) \times I(rr) \tag{13}$$

$$E(rl) = \alpha(l) \times I(rl) \tag{14}$$

If formulas (13) and (14) are substituted in formula (12), the following formula will be obtained:

$$K = 1/L \{\ln E(rr)/E(rl) + \ln \alpha(l)/\alpha(r)\} \tag{15}$$

If formula (15) is combined with formula (11), $\alpha(l)$ and $\alpha(r)$ will be eliminated to obtain the following formula:

$$K = 1/2L \{\ln E(ll)/E(lr) + \ln (E(rr)/E(rl)\}  \quad (16)$$

Thus, as shown in FIG. 2, two integrating spheres are set by a fixed distance L each other, and light propagating in opposite directions each other is projected into optical fiber in that segment to be measured alternatively. The ratio of the light amounts in the integrating spheres when the lights in the respective directions are projected in is measured, than the light transmission loss may be calculated using formula (16). The advantages of this method are that the constants $\alpha(l)$ and $\alpha(r)$ are eliminated. $\gamma(l)$ and $\gamma(r)$ will also, of course, be eliminated and the integrating spheres need not be in the form of ordinary integrating spheres but may be in any form, if they only condense light which radiates out of the optical fiber, and need not be in the same form as each other. Also, the photoelectric converting elements, amplifiers and indicators to be used need not be of the same performances.

It is emphasized that, although the principle of the above mentioned method of the present invention has been explained with reference to an optical fiber as an example, it is obvious that the material to be measured is not limited to only an optical fiber but can be any continuous or non-continuous optical material such as, for example, a thread, bar, tape, film, plate or block.

Further, the additional applications shown below are envisioned by utilizing the method of the present invention.

First, by continuously or intermittently running the material to be measured, the light transmission loss or an amount related to the light transmission loss can be measured without breaking the material.

Second, in the case of a comparatively short material to be measured, by alternately projecting light onto both end surfaces, it is possible to determine the light transmission loss with high sensitivity.

Third, since a non-contact measurement is possible, it is possible to measure the light transmission loss of a material which should not be stained or injured, such as an optical fiber material.

Figure 3:
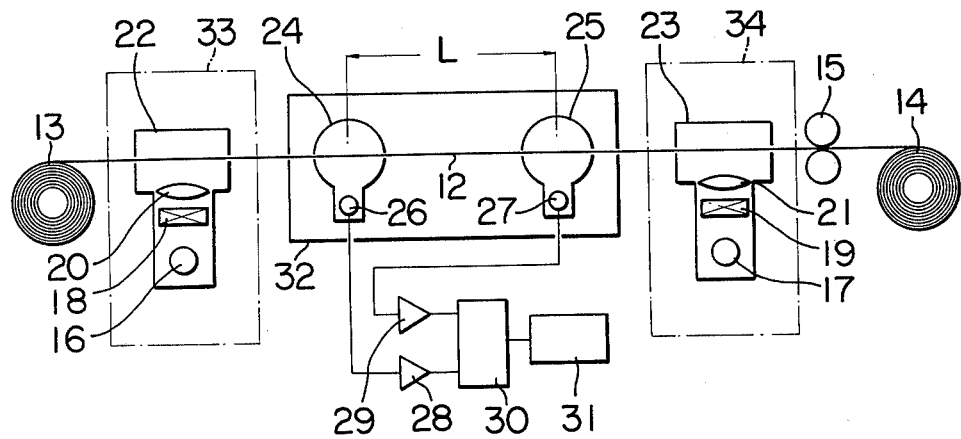
FIG. 3 is a partly vertically sectioned side view showing an embodiment of an apparatus to be used to work the present invention.

Fourth, by varying the wave length of the light source, it is possible to obtain the spectral characteristics of the light transmission loss. A preferred embodiment of the present invention will be explained with reference to FIG. 3. This embodiment makes it possible to continuously measure the light transmission loss of such optical material as an optical fiber without breaking it. In the drawing, 12 is an optical fiber, 13 is a bobbin of an original optical fiber, 14 is a bobbin having wound up a measured optical fiber, 15 is a pair of nipping rollers, 16 is a lamp (left), 17 is a lamp (right), 18 is a chopper (left), 19 is a chopper (right), 20 and 21 are lenses, 22 and 23 are light projecting part covers, 24 is an integrating sphere (left), 25 is an integrating sphere (right), 26 and 27 are photoelectric converting elements, 28 and 29 are amplifiers, 30 is an analogue computer, 31 is a recorder, 32 is a measuring part cover, 33 is a light projecting part (left) and 34 is a light projecting part (right). In such an apparatus, the optical fiber 12 comes out of the bobbin 13, is taken by the pair of nipping rollers 15 driven at a fixed velocity and is wound on the bobbin 14. The light projecting parts 33 and 34 substantially alternately project light into the optical fiber at a fixed period. It is preferable that the projecting period be shorter than the time required for the optical fiber 12 to pass through the integrating sphere 24 or 25 except in the case of a particularly homogeneous optical fiber. The choppers 18 and 19 alternately interrupt and pass the light. The chopper may be any of such types as an impeller, a prism or a Kerr cell. Further, the chopper need not always be used in the light projecting part. For example, by controlling the current source of the lamp, the light projection may be done intermittently. The lenses 20 and 21 are so arranged that the images of the lamps may be produced near the optical fiber 12. It is preferable that a material with a high reflection coefficient be used in the light projecting part covers 22 and 23 in order that the light projecting efficiency be maximized. Each of the integrating spheres 24 and 25 is preferably spherical, and covered on the inside surface with a high reflection coefficient but may be of any shape because, as described above, the shape of such integrating sphere may have no influence on the measurement. A photomultiplier tube is usually used for each of the photoelectric converting elements 26 and 27 but, if the sensitivity is high enough, anything will do. The amplifiers 28 and 29 are set as required. The analogue computer 30 is so constructed that it may be synchronized with the chopper of the projecting light source in order to calculate the light transmission loss by equation (16). The first and second terms in the parentheses of formula (16) may be alternately calculated and the average of them may be divided by the fiber length L. By connecting the recorder 31 with the analogue computer, it is possible to continuously record the light transmission loss of the optical fiber.

Having now fully described the invention, it will be apparent to one of ordinary skill in the art that many changes and modifications can be made thereto without departing from the spirit or scope of the invention as set forth herein. What is claimed as new and intended to be secured by Letters Patent is:

1. A method of measuring light transmission losses of optical material comprising the steps of:
    providing an optical material whose light transmission loss is to be measured and which has scattering elements that cause a fraction of any light transmitted through the optical material to be radiated out of the optical material;
    projecting light beams at two separate points alternately through a part of the optical material; and
    detecting the intensities of light radiated out of the optical mateiral at two separate points lying along the direction of transmission of said light beams in said part.

2. A method of measuring light transmission losses of optical materials according to claim 1 wherein said optical material is a continuous optical material.

3. A method of measuring light transmission losses of optical material according to claim 2 wherein said continuous optical material is an optical fiber.

4. A method of measuring light transmission losses of optical materials according to claim 2 wherein a light is projected from the two separate surface points of said material and the intensities of the radiated light beam from the two separate surface points of said material are measured.

5. A method of measuring light transmission losses of optical materials according to claim 4 wherein the intensities of radiated light are continuously detected while running the optical material.

* * * * *